US00PP20709P2

(12) United States Plant Patent
Hanes

(10) Patent No.: US PP20,709 P2
(45) Date of Patent: Feb. 2, 2010

(54) ***VERBENA* PLANT NAMED 'LAN UPBRIRO'**

(50) Latin Name: *Verbena hybrida*
Varietal Denomination: Lan Upbriro

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/313,827

(22) Filed: Nov. 25, 2008

(51) Int. Cl.
*A01H 5/00* (2006.01)

(52) U.S. Cl. ..... Plt./308

(58) Field of Classification Search ..... Plt./308
See application file for complete search history.

*Primary Examiner*—Annette H Para
(74) *Attorney, Agent, or Firm*—S. Matthew Edwards

(57) ABSTRACT

A new *Verbena* plant named 'Lan Upbriro' particularly distinguished by bold purple-red colored large flowers with mounding and outwardly spreading growth habit, vigorous, free-branching, medium green foliage and tolerance to powdery mildew.

1 Drawing Sheet

Latin name of the genus and species of the plant claimed: *Verbena hybrida.*

Varietal denomination: 'Lan Upbriro'.

BACKGROUND OF THE NEW PLANT

The present invention comprises a new *Verbena*, botanically known as *Verbena hybrida*, and hereinafter referred to by the variety name 'Lan Upbriro.'

'Lan Upbriro' is a product of a planned breeding program. The new cultivar 'Lan Upbriro' has bold purple-red colored large flowers with mounding and outwardly spreading growth habit, vigorous, free-branching, medium green foliage and tolerance to powdery mildew.

'Lan Upbriro' originated from a hybridization in a controlled breeding program in Gilroy, Calif. USA. The female parent was 'Lan Upmag,' U.S. Plant Pat. No. 18,983, with a magenta color. 'Lan Upmag' has lighter colored foliage, longer petioles and peduncles than 'Lan Upbriro.'

The male parent of 'Lan Upbriro' was 'Lan Upviot,' U.S. Plant Pat. No. 18,985, with purple-violet color. 'Lan Upviot' has smaller leaves, longer petioles and shorter peduncles than 'Lan Upbriro.'

'Lan Upbriro' was selected as one flowering plant within the progeny of the stated cross in February 2006 in a controlled environment in Gilroy, Calif. USA. The pollination took place in August 2005 and the seed sown in November 2005, all in Gilroy, Calif. USA.

The first act of asexual reproduction of 'Lan Upbriro' was accomplished when vegetative cuttings were taken from the initial selection in the February 2006 in a controlled environment in Gilroy, Calif. USA.

Horticultural examination of plants grown from cuttings of the plant initiated in February 2006 in Gilroy, Calif. USA, and continuing thereafter, has demonstrated that the combination of characteristics as herein disclosed for 'Lan Upbriro' are firmly fixed and are retained through successive generations of asexual reproduction.

'Lan Upbriro' has not been observed under all possible environmental conditions. The phenotype may vary significantly with variations in environment such as temperature, light intensity and day length.

A Plant Breeder's Right for this cultivar was applied for in Canada on Dec. 24, 2007. 'Lan Upbriro' has not been made publicly available more than one year prior to the filing of this application.

DESCRIPTION OF DRAWING

The accompanying photographic drawing shows typical flower and foliage characteristics of 'Lan Upbriro' with colors being as true as possible with an illustration of this type. The photographic drawing shows 3 flowering potted plants in a hanging basket of the new variety and a close-up of the flowers. The hanging basket was grown and photographed in Gilroy, Calif. USA, in July 2008 and the flower close-up was photographed in Boulder, Colo., in July 2007.

DETAILED BOTANICAL DESCRIPTION

The measurements were taken in Gilroy, Calif. USA, in March 2008 on plants that were growing in 4 inch plastic pots in a greenhouse trial. These plants were about 3 months old.

Color Chart used: Royal Horticultural Society Colour Chart (R.H.S.) 2001

BRIEF SUMMARY OF INVENTION

The following observations, measurements, and comparisons describe plants grown in Gilroy, Calif. USA. The following traits have been repeatedly observed and are determined to be basic characteristics of the new variety. The combination of these characteristics distinguishes this *Verbena* as a new and distinct variety.

TABLE 1

DIFFERENCES BETWEEN THE NEW VARIETY 'LAN UPBRIRO' AND A SIMILAR VARIETY

| | 'Lan Upbriro' | 'Lan Upmag' (U.S. Plant Pat. No. 18,983) |
|---|---|---|
| Flower color | RHS N74A-B | RHS N57A |
| Leaf/petiole size | Larger/shorter | Smaller/longer |
| Peduncle length | Shorter | Longer |

Plant:
*Plant habit.*—Mounding, outwardly spreading growth habit, vigorous, and free-branching.
*Plant height.*—15–17 cm.
*Plant width.*—18–24 cm.
Foliage:
*Arrangement.*—Opposite, simple.
*Immature, leaf color, upper surface.*—Little lighter than RHS 143A.
*Lower surface.*—Between RHS 144A and B.
*Mature, leaf color, upper surface.*—RHS 137A.
*Lower surface.*—Between RHS 144A and B.
*Length.*—3.9–4.1 cm.
*Width.*—2.6–2.9 cm.
*Shape.*—Ovate.
*Base shape.*—Obtuse.
*Apex shape.*—Acute.
*Margin.*—Irregularly, and slightly serrulate to crenate.
*Texture, upper surface.*—Hirsute; glandular hairs.
*Lower surface.*—Hirsute; glandular hairs of about RHS 70A and only along veins.
*Color of veins, upper surface.*—RHS 144A basally otherwise indistinct.
*Color of veins, lower surface.*—RHS 144B.
*Petioles color.*—RHS 144A to B.
*Petioles length.*—0.4–0.6 cm.
*Diameter of petiole.*—0.2 cm.
*Texture.*—Hirsute; pilose; glandular hairs of about RHS 70A.
Stem:
*Quantity of main branches per plant.*—8–10.
*Quantity of leaves per lateral branch.*—6–10.
*Color of stem.*—Little darker than RHS 144A.
*Length of stem.*—14–17 cm.
*Diameter.*—0.2–0.3 cm.
*Length of internodes.*—1.3–3.0 cm.
*Texture.*—Hirsute; pilose; glandular hairs of about RHS 70A.
Inflorescence:
*Type.*—Terminal Raceme.
*Blooming habit.*—Flowers continuously from spring through fall.
*Lastingness of individual blooms on the plant.*—5–7 days in the greenhouse.
*Fragrance.*—None.
*Number of inflorescences per plant.*—20–30 in various stages.
*Color of peduncle.*—RHS 144A.
*Length of peduncle.*—Most are between 2.5–3.0 cm; but a few are 5–6 cm.
*Peduncle diameter.*—0.2 cm.
*Texture.*—Hirsute; few pilose; glandular hairs of about RHS 70A.
*Horizontal diameter of inflorescence.*—5.5–6.0 cm.
*Depth of inflorescence.*—About 2.5 cm.
*Number of florets per inflorescence* (*including any buds at the time*).—16–21.
Bud (just before opening):
*Color.*—Between RHS N81A and B.
*Length.*—1.2–1.4 cm.
*Width.*—0.2–0.3 cm.
*Shape.*—Tubular.
Corolla:
*Form.*—Sessile; salverform, composed of 5 petals.
*Immature color, upper surface.*—Closest to RHS N74A but darker.
*Lower surface.*—RHS N74C ground color; RHS N155B basally; RHS N74B margins.
*Mature color, upper surface.*—Between RHS N74A and B ground color; RHS 79C at the throat. Then many florets fade to RHS N74B but lighter with irregular patches of between RHS N74C and RHS N155B some with about RHS N74C margins.
*Lower surface.*—RHS N74C to RHS N155B some with about RHS N74C margins.
*Floret diameter.*—2.0–2.2 cm.
*Length of petals.*—0.9–1.0 cm.
*Width of petals.*—0.85–0.9 cm.
*Petal shape.*—Obovate.
*Apex shape.*—Emarginate to cleft.
*Margin.*—Entire.
*Petal texture, upper surface.*—Papilloase; few glandular hairs around the corolla that are about RHS 72A.
*Lower surface.*—Slightly hirsute; glandular hairs more basally of about RHS 70A.
*Corolla tube length.*—2.0–2.2 cm.
*Corolla tube color inside.*—RHS N155B and RHS N78B; throat hairs of about RHS 156D.
*Tube color outside.*—RHS 155B basally; RHS N78A to B at the corolla flare.
*Corolla texture, inside.*—Glabrous.
*Outside.*—Glabrous basally; short glandular hairs towards apex of about RHS 70A.
Calyx:
*Type.*—Five sepals whose margins are fused to each other along their length, with a transparent membrane of less than 0.1 cm in width and with one smaller sepal attached to the base of the calyx.
*Color of sepals.*—RHS 137A with slight anthocyanins of about RHS N77A on the apex margin.
*Length of sepals.*—1.3–1.4 cm.
*Width of sepals.*—0.1–0.2 cm.
*Sepal shape.*—Linear.
*Apex shape.*—Acute.
*Margins.*—Entire.
*Texture, outer surface.*—Hirsute; few pilose; many glandular hairs of RHS 70A.
*Inner surface.*—Slightly hirsute.
Reproductive organs:
*Pistil.*—1.
*Length.*—1.8–1.9 cm.
*Style color.*—RHS 155B.
*Style length.*—1.3–1.6 cm.
*Stigma color.*—RHS 144A.
*Stamens.*—Anthers and filaments fused to upper half of corolla tube; four anthers with two pollen sacs per anther.
*Color of filaments.*—RHS 155C.
*Length filaments.*—0.2 cm.
*Length of anthers.*—0.1 cm.
*Anther color.*—RHS 10B.
*Color of pollen.*—RHS 10A.
*Pollen amount.*—Moderate.
*Fertility/seed set.*—Not observed on this hybrid.
Disease/pest resistance: Disease resistance or susceptibility has not been observed on this hybrid.

What is claimed is:

1. A new and distinct variety of *Verbena* plant named 'Lan Upbriro,' substantially as illustrated and described herein.

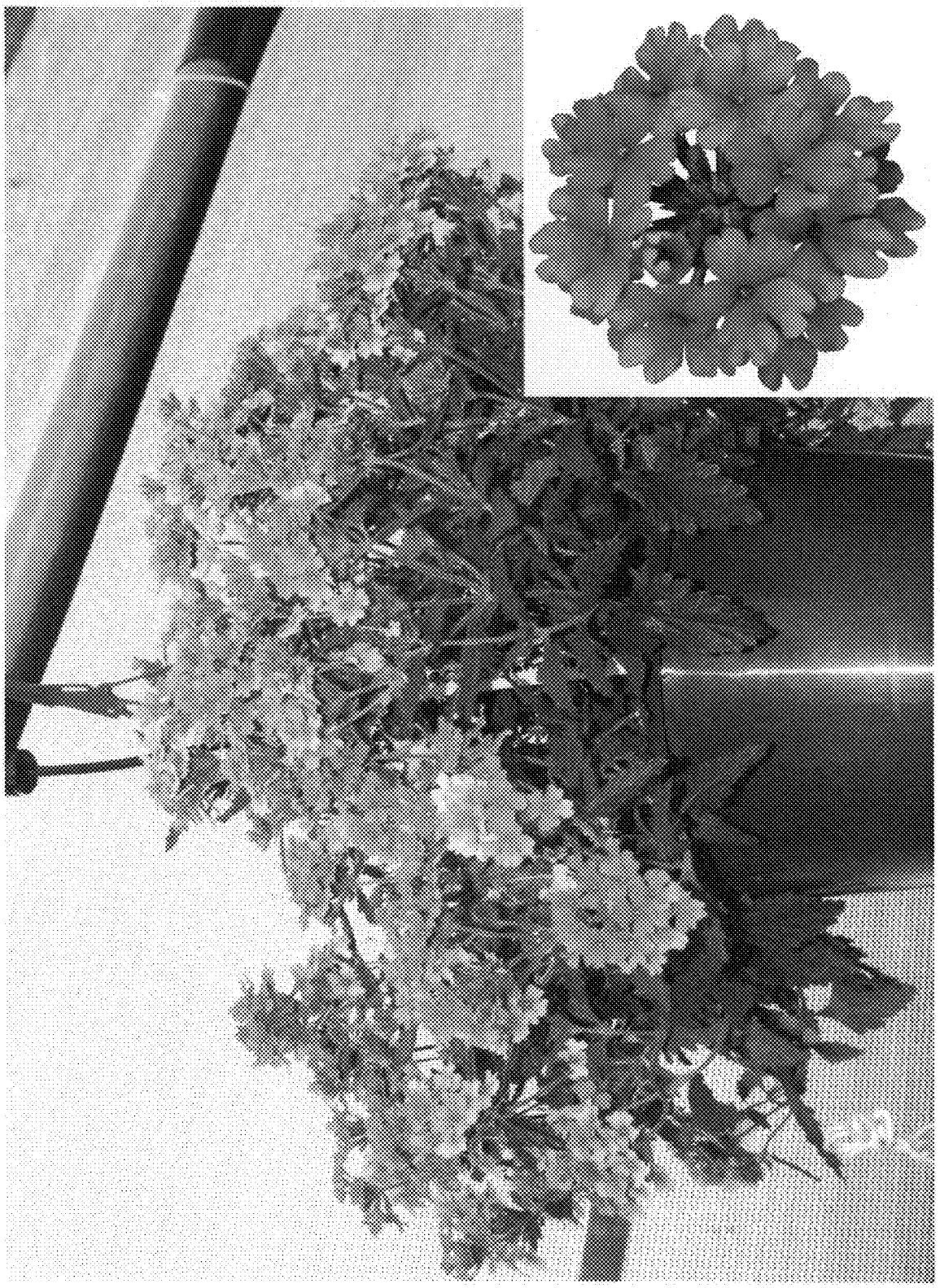

* * * * *